United States Patent [19]

Cesa et al.

[11] Patent Number: 4,868,061
[45] Date of Patent: Sep. 19, 1989

[54] OLEFINIC ARYL OXIME DERIVATIVES OF HYDANTOINS

[75] Inventors: Mark C. Cesa, South Euclid; James E. Rinz, University Heights; Teodora T. Kopp, Garfield Heights, all of Ohio

[73] Assignee: The Standard Oil Company, Cleveland, Ohio

[21] Appl. No.: 195,934

[22] Filed: May 19, 1988

[51] Int. Cl.$^4$ .......................................... C07D 403/04
[52] U.S. Cl. ................................... 526/258; 526/263; 548/309; 548/311; 548/312; 548/314
[58] Field of Search ................ 526/258, 263; 548/309, 548/311, 312, 314

[56] References Cited

U.S. PATENT DOCUMENTS 4,705,864  11/1987  Cesa et al. ......................... 548/311

Primary Examiner—Harold D. Anderson
Assistant Examiner—T. Mason
Attorney, Agent, or Firm—C. S. Lynch; D. J. Untener; L. W. Evans

[57] ABSTRACT

This invention relates to new compounds of the formula:

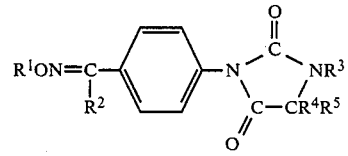

where each of $R^1$, $R^2$, $R^3$, $R^4$ and $R^5$ has zero to 10 C atoms, and no acetylenic unsaturation; each of $R^1$, $R^2$ and $R^3$ is independently selected from H and hydrocarbyl; each of $R^4$ and $R^5$ is independently selected from H, hydrocarbyl and hydrocarbyl substituted with a group selected from:
hydrocarbylcarbonylamino, di(hydrocarbylcarbonyl)amino, N-hydrocarbylcarbonyl(N-hydrocarbyl)amino, formylamino, diformylamino, and formyl(N-hydrocarbyl)amino, hydrocarbyloxy, hydrocarbylthio, formyl, formylthio, hydrocarbylcarbonyloxy, hydrocarbylcarbonylthio, hydrocarbyl carboxyl, hydrocarbyl thiocarboxyl, hydrocarbylamino, dihydrocarbylamino, hydrocarbylcarbonyl, 3-indolyl, 3-(1-hydrocarbyl)indolyl, 3-(1-hydrocarbylcarbonyl)indolyl, 3-(1-formyl)indolyl, carbamoyl, hydrocarbylcarbamoyl, dihydrocarbylcarbamoyl, 5-imidazolyl, 5-(3-hydrocarbyl)imidazolyl, 5-(3-hydrocarbylcarbonyl)imidazolyl, and 5-(3-formyl)imidazolyl, and where at least one of $R^1$, $R^2$, $R^3$, $R^4$ and $R^5$ contains olefinic unsaturation. The invention also relates to addition polymers of such compounds.

2 Claims, No Drawings

OLEFINIC ARYL OXIME DERIVATIVES OF HYDANTOINS

This invention relates to new compounds of the formula:

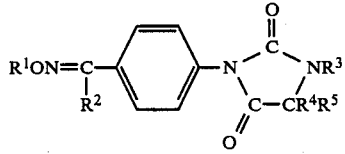

Formula 1 where each of $R^1$, $R^2$, $R^3$, $R^4$ and $R^5$ has zero to 10 C atoms, and no acetylenic unsaturation; each of $R^1$, $R^2$ and $R^3$ is independently selected from H and hydrocarbyl; each of $R^4$ and $R^5$ is independently selected from H, hydrocarbyl and hydrocarbyl substituted with a group selected from:
hydrocarbylcarbonylamino, di(hydrocarbylcarbonyl)amino, N-hydrocarbylcarbonyl(N-hydrocarbyl)amino, formylamino, diformylamino, and formyl(N-hydrocarbyl)amino, hydrocarbyloxy, hydrocarbylthio, formyl, formylthio, hydrocarbylcarbonyloxy, hydrocarbylcarbonylthio, hydrocarbyl carboxyl, hydrocarbyl thiocarboxyl, hydrocarbylamino, dihydrocarbylamino, hydrocarbylcarbonyl, 3-indolyl, 3-(1-hydrocarbyl)indolyl, 3-(1-hydrocarbylcarbonyl)indolyl, 3-(1-formyl)indolyl, carbamoyl, hydrocarbylcarbamoyl, dihydrocarbylcarbamoyl, 5-imidazolyl, 5-(3-hydrocarbyl)imidazolyl, 5-(3-hydrocarbylcarbonyl)imidazolyl, and 5-(3-formyl)imidazolyl,
and where at least one of $R^1$, $R^2$, $R^3$, $R^4$ and $R^5$ contains olefinic unsaturation. The invention also relates to addition polymers of such compounds.

These compounds are useful ultraviolet light absorbers. They can be used in plastic compositions to impart this property. It is believed that the excellent UV light absorption of these compounds is related to the fact that the compounds of the invention have the oxime, arene, and urea chromophores in conjugation. Such structures are believed to be novel.

The compounds of the invention all have high molar extinction coefficients, $\lambda_{max}=250-290$ nm, $\epsilon \geq 10^4$. In our work the particular solvent used in measuring the absorbance to determine the extinction coefficients is methanol.

The products of the present invention where $R^1$, $R^4$ or $R^5$ contains an olefinic group and where $R^2$ is H can be prepared by reacting the compound

Formula 2 where $R^6$ is phenyl or a $C_1$ to $C_6$ alkyl group, with an acetal of 4-aminobenzaldehyde derived from a $C_1$ to $C_6$ monalkanol or a $C_1$ to $C_6$ alkanediol, said reaction being carried out in a solvent such as dioxane, THF, diethyl ether, glymes and di-n-butyl ether in the presence of a non-nucleophilic base, and then reacting the product of such reaction with hydroxylamine hydrochloride in methanol as the solvent to obtain the compound

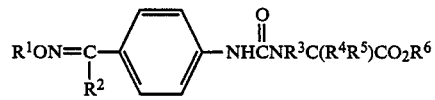

Formula 3 where $R^1$ and $R^2$ are H. The acetal can be prepared by first making the acetal of 4-nitrobenzaldehyde and then hydrogenating such acetal over platinum oxide catalyst to make the corresponding 4-aminobenzaldehyde, as illustrated in the specific examples.

The compound of Formula 3 is then reacted with sodium methoxide in methanol, maintaining a pH of about 10 or higher (usual range 9-11) while heating, usually by refluxing, usually for severl hours. The solvent is then removed under vacuum, leaving a product of Formula 1 where $R^1$ is H. This product is then treated with one molar equivalent (based on the amount of the Formula 1 product) of a strong base such as sodium hydride in one of the above solvents (dioxane, THF, etc.) followed by treatment with a $C_2$-$C_{10}$ olefinic halide such as allyl bromide or crotyl bromide, to prepare the product compound of this invention, of Formula 1, where $R^1$ contains olefinic unsaturation.

Products of the present invention where $R^1$, $R^4$ or $R^5$ contains an olefinic group and where $R^2$ is hydrocarbyl can be made by reacting the compound of Formula 2 with

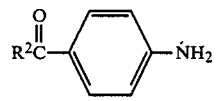

Formula 4 in one of the same solvents (dioxane, THF, etc.) to obtain

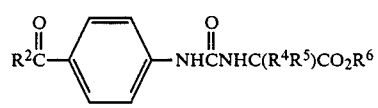

Formula 5 which is then separated from the solvent. This product is reacted in methanol solvent with hydroxylamine hydrochloride to obtain the compound of Formula 1 where $R^1$ is H. To prepare a product in which $R^1$ contains an olefinic group, this compound is then treated with one molar equivalent of sodium hydride in one of the above solvents (dioxane, THF, etc.) then with a $C_2$-$C_{10}$ olefinic halide such as allyl bromide or crotyl bromide, to prepare the product compound of Formula 1 where $R^1$ contains olefinic unsaturation.

To prepare products of the invention where both $R^1$ and $R^3$ contain olefinic unsaturation, the product of Formula 1 where $R^1$ and $R^3$ are H, prepared as described above with $R^2$ is H or hydrocarbyl, is treated with at least two molar equivalents of a strong base such as sodium hydride in one of the above solvents (dioxane, THF, etc.) followed by treatment with at least two equivalents of a $C_2$-$C_{10}$ olefinic halide such as allyl bromide or crotyl bromide. The solvent and unreacted reagent are removed to give a compound of the invention, of Formula 1, where $R^1$ and $R^3$ both contain olefinic unsaturation.

The products of the present invention where $R^3$, $R^4$ or $R^5$ contains an olefinic group can be prepared by reacting

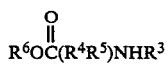

Formula 6 optionally prepared from the corresponding carboxylic acid by treatment with an alcohol $R^6OH$, with

Formula 7 in one of the same solvents (dioxane, THF, etc.) to prepare a compound of Formula 3, which is then separated from the solvent. This product is reacted in methanol solvent with hydroxylamine hydrochloride to obtain the compound of Formula 1.

The isocyanates of Formula 2 can be prepared by reacting the compound

Formula 8 or its salt with diphosgene in the manner illustrated in the examples herein.

In preparing the polymers of the present invention, a monomer of Formula 1 is polymerized in the presence of a polymerization catalyst. Suitable polymerization catalysts include, but are not restricted to, 2,2'-azobis-(isobutyro)nitrile (AIBN), di-(tert-butyl)peroxide, benzoyl peroxide, tert-butyl hydrogen peroxide, ammonium persulfate, potassium persulfate, and the like.

Two examples of the usefulness of the present compounds are as follows:

BLOW MOLDED LDPE BOTTLES 1 part substituted hydantoin compound or polymer is blended with 1000 parts low-density polyethylene in a plasticating screw extruder, pelletized, and blow molded to give a bottle which has substantially reduced UV transparency compared with a bottle made without the hydantoin compound or polymer.

POLYETHYLENE SHEET 1 part substituted hydantoin compound or polymer is blended with 1000 parts low-density polyethylene in a plasticating screw extruder and then extrusion blow molded into a thin film which exhibits substantially reduced UV transparency compared with film not containing the hydantoin compound or polymer.

The following examples are merely illustrative and are not to be considered as limiting.

EXAMPLE 1

4-Nitrobenzaldehyde ethylene glycol acetal is made as follows: A mixture of 75.5 g p-nitrobenzaldehyde, 100 mL ethylene glycol, and 2.5 g p-toluenesulfonic acid in 500 mL toluene is heated with stirring to reflux under $N_2$ for 5 hours in a 1000 mL round bottom flask equipped with a Dean-Stark trap and reflux condenser. During this time about 20 mL of a mixture of water and ethylene glycol is collected in the trap. The product mixture is washed with two 100 mL portions of saturated aqueous sodium bicarbonate solution and with 100 mL water. The organic layer is dried over $MgSO_4$, and the solvent is distilled off on a rotary evaporator. The resultant yellow solid is recrystallized from ethanol to give a yellow crystalline solid, mp. 87°–88° C., yield=-80–85%.

4-Aminobenzaldehyde ethylene glycol acetal is made as follows: A mixture of 19.5 g of p-nitrobenzaldehyde ethylene glycol acetal, 21.2 g trimethyl orthoformate, and 2 g $PtO_2$ in 250 mL anhydrous THF is placed in a 450 mL Parr stirred autoclave. The contents are purged with $N_2$, with the contents kept between 7° and 10° C. by external cooling. 100 psig $H_2$ was pressed in, and the reaction mixture is stirred. The reaction mixture warms to 20° C., and external cooling (ice bath) is maintained. The $H_2$ pressure is maintained at 100 psi by repressurization several times over a 14–18 minute period. The temperature then begins to drop, and little further drop in $H_2$ pressure is noted. The reaction mixture is stirred for a total of 45 minutes, after which time the reaction temperature returns to 7°–10° C. The autoclave is vented and opened, and the pale yellow product solution is filtered, dried over $CaSO_4$, refiltered, and distilled to dryness by rotary evaporator. The product p-aminobenzaldehyde ethylene glycol acetal, a nearly white solid, is collected in over 90% yield (mp.=71°-73° C.)

D,L-alanine methyl ester isocyanate is made as follows: 38.8 mL diphosgene is added dropwise over 1 hour to a mixture of 38.92 g DL-alanine methyl ester hydrochloride and 0.4 g activated charcoal in 400 mL dioxane under $N_2$. The reaction mixture warms to 75°–80° C. during this time. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the product is purified by fractional distillation to give pure DL-alanine methyl ester isocyanate in ~60% yield (b.p. 70° C., 10 mm Hg).

N-[4-hydroxyiminomethyl)phenyl]-N'-(1-methoxycarbonylethyl)urea is prepared as follows: A solution of 0.1 mol of p-aminobenzaldehyde ethylene glycol acetal in 100 mL of anhydrous THF is added dropwise over 10 minutes to a solution of 0.1 mol DL-alanine methyl ester isocyanate and 0.35 mol pyridine in 100 mL THF at room temperature under $N_2$. The yellow reaction mixture is stirred at room temperature for 2 hours. After ½ hour a yellow-orange precipitate begins to form. After 2 hours the solvent is removed by rotary evaporator to give an orange, semisolid mass. A solution of 0.11 mmoly hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. White crystals of product form after 2 hours of stirring. The crystals are isolated by filtration and dried overnight in a vacuum oven at 50°–55° C. The yield of product (mp 143°–145.5° C.) is 60%.

3-[4-hydroxyiminomethyl)phenyl]-5-methylhydantoin is made as follows: 14.15 g of N-[4-hydroxyiminomethyl)phenyl-N'-(1-methoxycarbonylethyl-)urea is dissolved in 300 mL of $CH_3OH$. The pH is adjusted to approximately 10.0 using 25% $NaOCH_3$ solution in $CH_3OH$ (appx. 4 mL). The solution is heated to reflux for 2.5 hours, after which time the solvent is removed under vacuum. The residue is washed with cold water and dried in vacuo to yield 9.10 g of the crude hydantoin. The hydantoin is purified by recrystallization from a 17:10:1 w:w:w solution of $CH_3OH$:$H_2O$:hydantoin, m.p. 215.0°–216.0° C. Elemental analysis: calcd. C 56.65, H 4.75, N 18.02; found C 56.63, H 4.72, N 18.04. $^{13}C$ NMR (acetone-$d_6$): δ 175, —NCOCH—; 156, —NCOC—; 148, —CH=NOH; 128, 133, 134, aryl; 53, —COCH($CH_3$)NH—; 18, —$CH_3$. $^1H$ NMR (acetone-$d_6$): δ 10.5 s, 1H, —CH=NOH; 8.2 s, 1H, —CH=NOH; 7.5 m, 4H, aryl; 4.35 quartet, 1H, —C;e,uns/H/ $CH_3$; 1.5 d, 3H, —CH$CH_3$. UV-visible ($CH_3OH$): $\lambda_{max}=262$ nm, $\epsilon=2.32\times 10^4$.

A solution of 0.01 mol of 3-[4-(hydroxyiminomethyl)phenyl]-5-methylhydantoin in diethyl ether is treated with 0.01 mol of sodium hydride. After hydrogen evolution stops, 0.011 mol of crotyl bromide is added. The reaction mixture is stirred for 2 hours. The reaction mixture is then poured into cold water, the layers are separated, and the aqueous layer is extracted with diethyl ether. The combined ether solutions are dried over $MgSO_4$ and filtered, and the solvent is removed by rotary evaporator to yield 3-[4-(crotyloxyiminomethyl)phenyl]-5-methylhydantoin.

EXAMPLE 2

38.8 mL diphosgene is added dropwise over 1 hour to a mixture of 35 g glycine methyl ester hydrochloride and 0.4 g activated charcoal in 400 mL dioxane under $N_2$. The reaction mixture warms to 80° C. during this time. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the product is purified by fractional distillation to give pure glycine methyl ester isocyanate in ~70% yield (bp 60° C., 13 mm Hg).

A solution of 0.1 mol of p-aminobenzaldehyde ethylene glycol acetal in 100 mL of anhydrous THF is added dropwise over 10 minutes to a solution of 0.1 mol glycine methyl ester isocyanate and 0.35 mol pyridine in 100 mL THF at room temperature under $N_2$. The yellow reaction mixture is stirred at room temperature for 2 hours. After ½ hour a yellow-orange precipitate begins to form. After 2 hours the solvent is removed by rotary evaporator to give an orange, semisolid mass. A solution of 0.11 mmol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. Pale yellow crystals of product form, which are isolated by filtration and dried overnight in a vacuum oven at 50°–55° C. The yield of crude product (mp 158°–161° C.): 70–75%. The product is purified by recrystallization from a 10:6:1 solution of $CH_3OH$:$H_2O$:compound. The product is washed with cold water and dried in a vacuum oven at 50° C. to give off-white crystals of N-[4-hydroxyiminomethyl)phenyl]-N'-methoxycarbonylmethylurea, mp. 167.5°–168.5° C. Elemental analysis: calcd. C 52.59, H 5.22, N 16.72; found C 52.38, H 5.16, N 16.65. $^1H$ NMR (acetone-$d_6$): δ10.15 s, 1H, —NOH; 8.4 s, 1H, —NH; 8.1 s/d, 1H, —CH=N; 7.55 bs, 4H, phenyl; 6.21 s/d, 1H, —NH—; 4.02 s/d, 2H, —$CH_2$—; 3.74 s, 3H, $CH_3O$—. $^{13}C$ NMR (acetone-$d_6$): δ172, —COO—; 156, —NCON—; 149, —CH; 50 N—; 119, 128, 142, phenyl; 52, $CH_3O$—; 42, —$CH_2$—. UV-vis ($CH_3OH$): $\lambda_{max}=279$ nm, $\epsilon=2.90\times 10^4$.

0.02 mol of this urea is dissolved in 300 mL of $CH_3OH$. The pH is adjusted to approximately 10.0 using 25% $NaOCH_3$ solution in $CH_3OH$. The solution is heated to reflux for 2.5 hours, after which time the solvent is removed in vacuo. The residue is washed with cold water and dried in vacuo to yield crude 3-[4-(hydroxyiminomethyl)phenyl]hydantoin. The hydantoin is purified by recrystallization from $CH_3OH$:$H_2O$.

A solution of 0.01 mol of 3-[4-(hydroxyiminomethyl)phenyl]-hydantoin in diethyl ether is treated with 0.01 mol of sodium hydride. After hydrogen evolution stops, 0.011 mol of allyl bromide is added. The reaction mixture is stirred for 2 hours. The reaction mixture is then poured into cold water, the layers are separated, and the aqueous layer is extracted with diethyl ether. The combined ether solutions are dried over $MgSO_4$ and filtered, and the solvent is removed by rotary evaporator to yeild 3-[4-(allyloxyiminomethyl)phenyl]hydantoin.

EXAMPLE 3

9.7 mL diphosgene is added dropwise over 50 minutes to a mixture of 12.85 g diemthyl aminomalonate hydrochloride and 0.1 g activated charcoal in 25 mL dioxane under $N_2$. The reaction mixture warms to 75°–80° C. during this time. The reaction mixture is then heated and stirred at reflux for 2½ hours. The reaction mixture is then cooled, filtered, and concentrated to dryness by rotary evaporator, keeping exposure to moisture to a minimum. The crude product is purified by fractional distillation (bp 80°–85° C., <1 mm Hg) to give pure dimethyl isocyanatomalonate in >80% yield.

A solution of 0.1 mol of p-aminobenaldehyde ethylene glycol acetal in 100 mL of anhydrous THF is added dropwise over 10 minutes to a solution of 0.1 mol dimethyl aminomalonate isocyanate and 0.35 mol pyridine in 100 mL THF at room temperature under $N_2$. The yellow reaction mixture is stirred at room temperature for 2 hours. After ½ hour a yellow-orange precipitate begins to form. After 2 hours the solvent is removed by rotary evaportor to give an orange, semisolid mass. A solution of 0.11 mmol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaportor, and water is added. White crystals of product form, which were isolated by filtration and dried overnight in a vacuum oven at 50°–55° C. The yield of crude product (mp 164°–166° C.): 75–80%.

The product is purified by multiple extraction with ethanol until the washings are no longer yellow. White crystals of 3-[4-(hydroxyiminomethyl)phenyl]-N'-bis(methyloxycarbonyl)methylurea result, m.p. 161.5°–162.5° C. Elemental analysis: calcd. c 50.49, H, 4.89, N, 13.59; found C 50.88, H, 4.90, N 13.52. $^1H$ NMR (acetone-$d_6$): δ10.95 s, 1H, —NOH; 9.1 s, 1H, —NH; 7.55 bs, 4H, phenyl; 7.15 d, 1H, —NH; 5.15 s/d, 1H, —CH; 3.80 s, 3H, $CH_3O$—. $^{13}C$ NMR (acetone-$d_6$): δ168, —COO—; 155, —NCON—; 148, —CH=N—; 118, 128, 142, phenyl; 58, $CH_3O$—; 53, —$CH_2$—. UV-vis ($CH_3OH$): $\lambda_{max}=276$ nm, $\epsilon=3.06\times 10^4$.

0.02 mol of this urea is dissolved in 300 mL of $CH_3OH$. The pH is adjusted to approximately 10.0 using 25% $NaOCH_3$ solution in $CH_3OH$. The solution is heated to reflux for 2.5 hours, after which time the solvent is removed in vacuo. The residue is washed with cold water and dried in vacuo to yield crude 3-[4-(hydroxyiminomethyl)phenyl]-5-methoxycarbonylhydantoin. The hydantoin is purified by recrystallization from $CH_3OH:H_2O$.

A solution of 0.01 mol of 3-[4-(hydroxyiminomethyl)phenyl]-5-methoxycarbonylhydantoin in diethyl ether is treated with 0.01 mol of sodium hydride. After hydrogen evolution stops, 0.011 mol of allyl bromide is added. The reaction mixture is stirred for 2 hours. The reaction mixture is then poured into cold water, the layers are separated, and the aqueous layer is extracted with diethyl ether. The combined ether solutions are dried over $MgSO_4$ and filtered, and the solvent is removed by rotary evaporator to yield 3-[4-(allyloxyiminomethyl)phenyl]-5-methoxycarbonylhydantoin.

EXAMPLES 4–15

For the compounds in Table 1, the following procedure is used: 0.35 mol diphosgene is added dropwise over 1 hour to a mixture of 0.28 mol of amino acid methyl ester and 0.4 g activated charcoal in 400 mL dioxane under $N_2$. The reaction mixture is then heated and stirred at reflux for 2½ hours. The reaction mixture is then cooled, filtered, and concentrated to dryness by rotary evaporator, keeping exposure to moisture to a minimum. The crude product is redissolved in 100 mL THF, and the pH of the solution is adjusted to 5.5–6.0 by addition of pyridine. The product mixture is then filtered, and the product is purified by fractional distillation to give the amino acid methyl ester isocyanate.

A solution of 0.1 mol of p-aminobenzaldehyde ethylene glycol acetal in 100 mL of anhydrous THF is added dropwise over 10 minutes to a solution of 0.1 mol of the amino acid methyl ester isocyanate and 0.35 mol pyridine in 100 mL THF at room temperature under $N_2$. The reaction mixture is stirred at room temperature for 2 hours. After 2 hours the solvent is removed by rotary evaporator. A solution of 0.11 mmol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. The product is isolated by filtration and dried in vacuo.

0.02 mol of this urea is dissolved in 300 mL of $CH_3OH$. The pH is adjusted to approximately 10.0 using $NaOCH_3$ solution in $CH_3OH$. The solution is heated to reflux for 2.5 hours, after which time the solvent is removed in vacuo. The residue is washed with cold water and dried in vacuo to yield the crude 3-[4-hydroxyiminomethyl)phenyl]hydantoin. The hydantoin is purified by recrystallization from $CH_3OH:H_2O$.

A solution of 0.01 mol of the 3-[4-hydroxyiminomethyl)phenyl]hydantoin in diethyl ether is treated with 0.01 mol of sodium hydride. After hydrogen evolution stops, 0.011 mol of allyl bromide is added. The reaction mixture is stirred for 2 hours. The reaction mixture is then poured into cold water, the layers are separated, and the aqueous layer is extracted with diethyl ether. The combined ether solutions are dried over $MgSO_4$ and filtered, and the solvent is removed by rotary evaporator to yield the 3-[4-(alloyloxyiminomethyl)phenyl]hydantoin.

TABLE 1

| Example | Amino Acid Methyl Ester | Product |
| --- | --- | --- |
| 4 | valine | 3-[4-(allyloxyiminomethyl)phenyl]-5-isopropylhydantoin |
| 5 | leucine | 3-[4-(allyloxyiminomethyl)phenyl]-5-isobutlyhydantoin |
| 6 | isoleucine | 3-[4-(allyloxyiminomethyl)phenyl]-5-sec-butylhydantoin |
| 7 | phenylalanine | 3-[4-(allyloxyiminomethyl)phenyl]-5-benzylhydantoin |
| 8 | methionine | 3-[4-(allyloxyiminomethyl)phenyl]-5-(2-methylthioethyl)hydantion |
| 9 | O—acetylserine | 3-[4-(allyloxyiminomethyl)phenyl]-5-acetyloxymethylhydantoin |
| 10 | O—acetylthreonine | 3-[4-(allyloxyiminomethyl)phenyl]-5-(1-acetyloxyethyl)hydantoin |
| 11 | S—acetylcysteine | 3-[4-(allyloxyiminomethyl)phenyl]-5-acetylthiomethylhydantoin |
| 12 | (N—acetyl-3-indolyl)alanine | 3-[4-(allyloxyiminomethyl)phenyl]-5-(1-acetyl-3-indolyl)methylhydantoin |
| 13 | O—acetyltyrosine | 3-[4-(allyloxyiminomethyl)phenyl]-5-(4-acetyloxyphenyl)methylhydantoin |
| 14 | aspartic acid dimethyl ester | 3-[4-(allyloxyiminomethyl)phenyl]-5-methoxycarbonylmethylhydantoin |
| 15 | glutamic acid dimethyl ester | 3-[4-(allyloxyiminomethyl)phenyl]-5-(2-methyoxycarbonylethyl)hydantoin |

EXAMPLE 16

3-[4-(1-Hydroxyiminoethyl)phenyl]hydantoin is made as follows: A solution of 2.7 g p-aminoacetophenone in 40 mL THF is added dropwise to a solution of 2.3 g glycine methyl ester isocyanate and 5 mL pyridine in 40 mL THF, and the reaction mixture is stirred for 3 hours. The solvent is then removed by rotary evaporator to leave an off-white solid. The solid is dispersed in 50 mL $CH_3OH$, and 1.53 g hydroxylamine hydrochloride and 6.4 g trimethyl orthoformate are added. The reaction mixture is heated to reflux for 1 hour. The solvent is removed by rotary evaporator to leave an orange oil. Addition of water to the oil results in formation of off-white crystals. The crystals are treated again with 1.0 g hydroxylamine hydrochloride and 3.0 g trimethyl orthoformate in 50 mL $CH_3OH$ at reflux for 1 hour. The product mixture is then treated with $NaOCH_3$ in $CH_3OH$ to adjust the pH of the solution to 7. The product mixture is then concentrated by rotary evaporator, water is added, and the solid which forms (m.p. 179°–181° C. dec.) is shown by $^1H$ NMR spectroscopy (acetone-$d_6$/DMSO-$d_6$) to contain the hydantoin product. $^1H$ NMR resonances assignable to the hydantoin include: δ 4.1 s, 2H, —CO$\underline{CH_2}$— NH—; 2.25 s, 3H, HON=C(C$\underline{H_3}$)—.

A solution of 0.01 mol of 3-[4-(1-hydroxyiminoethyl)phenyl]hydantoin in diethyl ether is treated with 0.01 mol of sodium hydride. After hydrogen evolution stops, 0.011 mol of crotyl bromide is added. The reaction mixture is stirred for 2 hours. The reaction mixture is then poured into cold water, the layers are separated, and the aqueous layer is extracted with diethyl ether. The combined ether solutions are dried over $MgSO_4$ and filtered, and the solvent is removed by rotary evaporator to yield 3-[4-(1-crotyloxyiminoethyl)phenyl]hydantoin.

The foregoing procedure to prepare the hydroxyiminoethyl hydantoin is repeated except that the step of adjusting the pH is omitted. The solid product has a m.p. of 179°–181° C. (dec.) and is shown by NMR spectroscopy to be pure N-[4-(1-hydroxyiminoethyl)phenyl]-N'-methoxycarbonylmethylurea.

EXAMPLES 17–30

For the compounds in Table 2, the following procedure is used: A solution of 0.02 mol p-aminoacetophenone in 40 mL THF is added dropwise to a solution of 0.02 mol of amino acid ester isocyanate and 5 mL pyridine in 40 mL THF, and the reaction mixture is stirred for 3 hours. The solvent is then removed by rotary evaporator. The residue is dispersed in 50 mL CH₃OH, and 1.53 g hydroxylamine hydrochloride and 6.4 g trimethyl orthoformate are added. The reaction mixture is heated to reflux for 1 hour. The solvent is removed by rotary evaporator to give the N-[4-(1-hydroxyiminoethyl)phenyl]urea.

0.02 mol of this urea is dissolved in 300 mL of CH₃OH. The pH is adjusted to approximately 10.0 using 25% NaOCH₃ solution in CH₃OH. The solution is heated to reflux for 2.5 hours, after which time the solvent is removed in vacuo. The residue is washed with cold water and dried in vacuo to yield the crude 3-[4-(1-hydroxyiminoethyl)phenyl]hydantoin. The hydantoin is purified by recrystallization from CH₃OH:H₂O.

A solution of 0.01 mol of the 3-[4-(hydroxyiminoethyl)phenyl]hydantoin in diethyl ether is treated with 0.01 mol of sodium hydride. After hydrogen evolution stops, 0.011 mol of allyl bromide is added. The reaction mixture is stirred for 2 hours. The reaction mixture is then poured into cold water, the layers are separated, and the aqueous layer is extracted with diethyl ether. The combined ether solutions are dried over MgSO₄ and filtered, and the solvent is removed by rotary evaporator to yield the product 3-[4-(1-allyloxyiminoethyl)phenyl]hydantoin.

EXAMPLE 31

A solution of 0.01 mol of 3-[4-(hydroxyiminomethyl)phenyl]hydantoin in diethyl ether is treated with 0.02 mol of sodium hydride. After hydrogen evolution stops, 0.022 mol of allyl bromide is added. The reaction mixture is stirred for 2 hours. The reaction mixture is then poured into cold water, the layers are separated, and the aqueous layer is extracted with diethyl ether. The combined ether solutions are dried over MgSO₄ and filtered, and the solvent is removed by rotary evaporator to yield 1-allyl-3-[4-(allyloxyiminomethyl)phenyl]hydantoin.

TABLE 2

| Example | Amino Acid Methyl Ester Isocyanate | Product |
|---|---|---|
| 17 | alanine | 3-[4-(1-allyloxyiminoethyl)phenyl]-5-methylhydantoin |
| 18 | valine | 3-[4-(1-allyloxyiminoethyl)phenyl]-5-isopropylhydantoin |
| 19 | leucine | 3-[4-(1-allyloxyiminoethyl)phenyl]-5-isobutylhydantoin |
| 20 | isoleucine | 3-[4-(1-allyloxyiminoethyl)phenyl]-5-sec-butylhydantoin |
| 21 | phenylalanine | 3-[4-(1-allyloxyiminoethyl)phenyl]-5-benzylhydantoin |
| 22 | (N—acetyl-3-indolyl)alanine | 3-[4-(1-allyloxyiminoethyl)phenyl]-5-(1-acetyl-3-indolyl)methylhydantoin |
| 23 | methionine | 3-[4-(1-allyloxyiminoethyl)phenyl]-5-(2-methylthioethyl)hydantoin |
| 24 | O—acetylserine | 3-[4-(1-allyloxyiminoethyl)phenyl)]-5-acetyloxymethylhydantoin |
| 25 | O—acetylthreonine | 3-[4-(1-allyloxyiminoethyl)phenyl]-5-(1-acetyloxyethyl)hydantoin |
| 26 | S—acetylcysteine | 3-[4-(1-allyloxyiminoethyl)phenyl]-5-acetylthiomethylhydantoin |
| 27 | O—acetyltyrosine | 3-[4-(1-allyloxyiminoethyl)phenyl]-5-(4-acetyloxyphenyl)methylhydantoin |
| 28 | aspartic acid dimethyl ester | 3-[4-(1-allyloxyiminoethyl)phenyl]-5-methoxycarbonylmethylhydantoin |
| 29 | glutamic acid dimethyl ester | 3-[4-(1-allyloxyiminoethyl)phenyl]-5-(2-methoxycarbonylethyl)hydantoin |
| 30 | aminomalonic acid dimethyl ester | 3-[4-(1-allyloxyiminomethyl)phenyl]-5-methoxycarbonyl hydantoin |

EXAMPLES 32–45

For the compounds in Table 3, the following procedure is used: A solution of 0.01 mol of the 3-[4-(hydroxyiminomethyl)phenyl]hydantoin in diethyl ether is treated with 0.02 mol of sodium hydride. After hydrogen evolution stops, 0.022 mol of allyl bromide is added. The reaction mixture is stirred for 2 hours. The reaction mixture is then poured into cold water, the layers are separated, and the aqueous layer is extracted with diethyl ether. The combined ether solutions are dried over MgSO₄ and filtered, and the solvent is removed by rotary evaporator to yield the product 1-allyl-3-[4-(1-allyloxyiminoethyl)phenyl]hydantoin.

EXAMPLE 46

A solution of 0.01 mol of 3-[4-(1-hydroxyiminoethyl)phenyl]hydantoin in diethyl ether is treated with 0.02 mol of sodium hydride. After hydrogen evolution stops, 0.022 mol of crotyl bromide is added. The reaction mixture is stirred for 2 hours. The reaction mixture is then poured into cold water, the layers are separated, and the aqueous layer is extracted with diethyl ether. The combined ether solutions are dried over MgSO₄ and filtered, and the solvent is removed by rotary evaporator to yield 1-allyl-3-[4-(1-crotyloxyiminoethyl)phenyl]hydantoin.

TABLE 3

| Example | Amino Acid Methyl Ester Isocyanate | Product |
|---|---|---|
| 32 | alanine | 1-allyl-3-[4-(allyloxyiminomethyl)phenyl]-5-methylhydantoin |
| 33 | valine | 1-allyl-3-[4-(allyloxyiminomethyl)phenyl]-5-isopropylhydantoin |
| 34 | leucine | 1-allyl-3-[4-(allyloxyiminomethyl)phenyl]-5-isobutylhydantoin |
| 35 | isoleucine | 1-allyl-3-[4-(allyloxyiminomethyl)phenyl]-5-sec-butylhydantoin |
| 36 | phenylalanine | 1-allyl-3-[4-(allyloxyiminomethyl)phenyl]-5-benzylhydantoin |
| 37 | (N—acetyl-3-indolyl)alanine | 1-allyl-3-[4-(allyloxyiminomethyl)phenyl]-5-(1-acetyl-3-indolyl)methylhydantoin |
| 38 | methionine | 1-allyl-3-[4-(allyloxyiminomethyl)phenyl]-5-(2-methylthioethyl)hydantoin |
| 39 | O—acetylserine | 1-allyl-3-[4-(allyloxyiminomethyl)phenyl]-5-acetyloxymethylhydantoin |
| 40 | O—acetylthreonine | 1-allyl-3-[4-(allyloxyiminomethyl)phenyl]-5-(1-acetyloxyethyl)hydantoin |

TABLE 3-continued

| Example | Amino Acid Methyl Ester Isocyanate | Product |
| --- | --- | --- |
| 41 | S—acetylcysteine | 1-allyl-3-[4-(allyloxyiminomethyl)phenyl]-5-acetylthiomethylhydantoin |
| 42 | O—acetyltyrosine | 1-allyl-3-[4-(allyloxyiminomethyl)phenyl]-5-(4-acetyloxyphenyl)methylhydantoin |
| 43 | aspartic acid dimethyl ester | 1-allyl-3-[4-(allyloxyiminomethyl)phenyl]-5-methoxycarbonylmethylhydantoin |
| 44 | glutamic acid dimethyl ester | 1-allyl-3-[4-(allyloxyiminomethyl)phenyl]-5-(2-methoxycarbonylethyl)hydantoin |
| 45 | aminomalonic acid dimethyl ester | 1-allyl-3-[4-(allyloxyiminomethyl)phenyl]-5-methoxycarbonylhydantoin |

EXAMPLES 47–60

For the compounds in Table 4, the following procedure is used: A solution of 0.01 mol of 3-[4-(1-hydroxyiminoethyl)phenyl]hydantoin in diethyl ether is treated with 0.02 mol of sodium hydride. After hydrogen evolution stops, 0.022 mol of allyl bromide is added. The reaction mixture is stirred for 2 hours. The reaction mixture is then poured into cold water, the layers are separated, and the aqueous layer is extracted with diethyl ether. The combined ether solutions are dried over $MgSO_4$ and filtered, and the solvent is removed by rotary evaporator to yield the product 1-allyl-3-[4-(1-allyloxyiminoethyl)phenyl]hydantoin.

TABLE 4

| Example | Amino Acid Methyl Ester Isocyanate | Product |
| --- | --- | --- |
| 47 | alanine | 1-allyl-3-[4-(1-allyloxyiminoethyl)phenyl]-5-methylhydantoin |
| 48 | valine | 1-allyl-3-[4-(1-allyloxyiminoethyl)phenyl]-5-isopropylhydantoin |
| 49 | leucine | 1-allyl-3-[4-(1-allyloxyiminoethyl)phenyl]-5-isobutylhydantoin |
| 50 | isoleucine | 1-allyl-3-[4-(1-allyloxyiminoethyl)phenyl]-5-sec-butylhydantoin |
| 51 | phenylalanine | 1-allyl-3-[4-(1-allyloxyiminoethyl)phenyl]-5-benzylhydantoin |
| 52 | (N—acetyl-3-indolyl)alanine | 1-allyl-3-[4-(1-allyloxyiminoethyl)phenyl]-5-(1-acetyl-3-indolyl)methylhydantoin |
| 53 | methionine | 1-allyl-3-[4-(1-allyloxyiminoethyl)phenyl]-5-(2-methylthioethyl)hydantoin |
| 54 | O—acetylserine | 1-allyl-3-[4-(1-allyloxyiminoethyl)phenyl]-5-acetyloxymethylhydantoin |
| 55 | O—acetylthreonine | 1-allyl-3-[4-(1-allyloxyiminoethyl)phenyl]-5-(1-acetyloxyethyl)hydantoin |
| 56 | S—acetylcysteine | 1-allyl-3-[4-(1-allyloxyiminoethyl)phenyl]-5-acetylthiomethylhydantoin |
| 57 | O—acetyltyrosine | 1-allyl-3-[4-(1-allyloxyiminoethyl)phenyl]-5-(4-acetyloxyphenyl)methylhydantoin |
| 58 | aspartic acid dimethyl ester | 1-allyl-3-[4-(1-allyloxyiminoethyl)phenyl]-5-methoxycarbonylmethylhydantoin |
| 59 | glutamic acid dimethyl ester | 1-allyl-3-[4-(1-allyloxyiminoethyl)phenyl]-5-(2-methoxycarbonylethyl)hydantoin |
| 60 | aminomalonic acid dimethyl ester | 1-allyl-3-[4-(1-allyloxyiminoethyl)phenyl]-5-methoxycarbonylhydantoin |

EXAMPLE 61

0.35 mol diphosgene is added dropwise over 1 hour to a mixture of 0.28 mol of methyl 2-amino-4-pentenoate, prepared as described by D. Ferroud, J. P. Genet, and R. Kiolle in *Tetrahedron Letters,* 1986, 27, 23–26, and 0.4 g activated charcoal in 400 mL dioxane under $N_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the product is purified by fractional distillation to give methyl 2-isocyanato-4-pentenoate.

A solution of 0.1 mol of p-aminobenzaldehyde ethylene glycol acetal in 100 mL of anhydrous THF is added dropwise over 10 minutes to a solution of 0.1 mol of methyl 2-isocyanato-4-pentenoate and 0.35 mol pyridine in 100 mL THF at room temperature under $N_2$. The reaction mixture is stirred at room temperature for 2 hours. After 2 hours the solvent is removed by rotary evaporator. A solution of 0.11 mmol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. The product, N-[4-(hydroxyiminomethyl)phenyl]-N'-[1-(1-methoxycarbonyl)-3-butenyl]urea, is isolated by filtration and dried in vacuo.

0.02 mol of this urea is dissolved in 300 mL of $CH_3OH$. The pH is adjusted to approximately 10.0 using 25% $NaOCH_3$ solution in $CH_3OH$. The solution is heated to reflux for 2.5 hours, after which time the solvent is removed in vacuo. The residue is washed with cold water and dried in vacuo to yield crude 3-[4-(hydroxyiminomethyl)phenyl]-5-allylhydantoin. The hydantoin is purified by recrystallization from $CH_3OH:H_2O$.

EXAMPLE 62

0.35 mol diphosgene is added dropwise over 1 hour to a mixture of 0.28 mol of methyl 2-amino-4-methyl-4-pentenoate, prepared as described by D. Ferroud, J. P. Genet, and R. Kiolle in *Tetrahedron Letters,* 1986, 27, 23–26, and 0.4 g activated charcoal in 400 mL dioxane under $N_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the product is purified by fractional distillation to give methyl 2-isocyanato-4-methyl-4-pentenoate.

A solution of 0.1 mol of p-aminobenzaldehyde ethylene glycol acetal in 100 mL of anhydrous THF is added dropwise over 10 minutes to a solution of 0.1 mol of methyl 2-isocyanato-4-methyl-4-pentenoate and 0.35 mol pyridine in 100 mL THF at room temperature under $N_2$. The reaction mixture is stirred at room temperature for 2 hours. After 2 hours the solvent is removed by rotary evaporator. A solution of 0.11 mmol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. The product, N-[4-(hydroxyiminomethyl)phenyl]-N'-[1-(1-methoxycarbonyl)-3-methyl-3-butenyl]urea, is isolated by filtration and dried in vacuo.

0.02 mol of this urea is dissolved in 300 mL of $CH_3OH$. The pH is adjusted to approximately 10.0 using 25% $NaOCH_3$ solution in $CH_3OH$. The solution is heated to reflux for 2.5 hours, after which time the solvent is removed in vacuo. The residue is washed with cold water and dried in vacuo to yield crude 3-[4-(hydroxyiminomethyl)phenyl]-5-(2-methylallyl)hydantoin. The hydantoin is purified by recrystallization from $CH_3OH:H_2O$.

EXAMPLE 63

0.35 mol diphosgene is added dropwise over 1 hour to a mixture of 0.28 mol of methyl 2-amino-5-phenyl-4-pentenoate, prepared as described by D. Ferroud, J. P. Genet, and R. Kiolle in *Tetrahedron Letters,* 1986, 27, 23–26, and 0.4 g activated charcoal in 400 mL dioxane under $N_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the product is purified by fractional distillation to give methyl 2-isocyanato-5-phenyl-4-pentenoate.

A solution of 0.1 mol of p-aminobenzaldehyde ethylene glycol acetal in 10 mL of anhydrous THF is added dropwise over 10 minutes to a solution of 0.1 mol of methyl 2-isocyanato-5-phenyl-4-pentenoate and 0.35 mol pyridine in 100 mL THF at room temperature under $N_2$. The reaction mixture is stirred at room temperature for 2 hours. After 2 hours the solvent is removed by rotary evaporator. A solution of 0.11 mmol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. The product, N-[4-(hydroxyiminomethyl)phenyl]-N'-[1-(1-methoxycarbonyl)-4-phenyl-3-butenyl]urea, is isolated by filtration and dried in vacuo.

0.02 mol of this urea is dissolved in 300 mL of $CH_3OH$. The pH is adjusted to approximately 10.0 using 25% $NaOCH_3$ solution in $CH_3OH$. The solution is heated to reflux for 2.5 hours, after which time the solvent is removed in vacuo. The residue is washed with cold water and dried in vacuo to yield crude 3-[4-(hydroxyiminomethyl)phenyl]-5-(3-phenylallyl)hydantoin. The hydantoin is purified by recrystallization from $CH_3OH:H_2O$.

EXAMPLE 64

0.35 mol diphosgene is added dropwise over 1 hour to a mixture of 0.28 mol of methyl 2-amino-6-acetyloxy-4-hexenoate, prepared as described by D. Ferroud, J. P. Genet, and R. Kiolle in *Tetrahedron Letters,* 1986, 27, 23–26, and 0.4 g activated charcoal in 400 mL dioxane under $N_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the product is purified by fractional distillation to give methyl 2-isocyanato-6-acetyloxy-4-hexenoate.

A solution of 0.1 mol of p-aminobenzaldehyde ethylene glycol acetal in 100 mL of anhydrous THF is added dropwise over 10 minutes to a solution of 0.1 mol of methyl 2-isocyanato-6-acetyloxy-4-hexenoate and 0.35 mol pyridine in 100 mL THF at room temperature under $N_2$. The reaction mixture is stirred at room temperature for 2 hours. After 2 hours the solvent is removed by rotary evaporator. A solution of 0.11 mmol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. The product, N-[4-(hydroxyiminomethyl)phenyl]-N'-[1-(1-methoxycarbonyl)-5-acetyloxy-3-pentenyl]urea, is isolated by filtration and dried in vacuo.

0.02 mol of this urea is dissolved in 300 mL of $CH_3OH$. The pH is adjusted to approximately 10.0 using 25% $NaOCH_3$ solution in $CH_3OH$. The solution is heated to reflux for 2.5 hours, after which time the solvent is removed in vacuo. The residue is washed with cold water and dried in vacuo to yield crude 3-[4-(hydroxyiminomethyl)phenyl]-5-(4-acetyloxy-2-butenyl)hydantoin. The hydantoin is purified by recrystallization from $CH_3OH:H_2O$.

EXAMPLE 65

A solution of 0.02 mol p-aminoacetophenone in 40 mL THF is added dropwise to a solution of 0.02 mol of methyl 2-isocyanato-4-pentenoate and 5 mL pyridine in 40 mL THF, and the reaction mixture is stirred for 3 hours. The solvent is then removed by rotary evaporator. The residue is dispersed in 50 mL $CH_3OH$, and 1.53 g hydroxylamine hydrochloride and 6.4 g trimethyl orthoformate are added. The reaction mixture is heated to reflux for 1 hour. The solvent is removed by rotary evaporator to give the product, N-[4-(1-hydroxyiminoethyl)phenyl]-N'-[1-(1-methoxycarbonyl)-3-butenyl]urea.

0.02 mol of this urea is dissolved in 300 mL of $CH_3OH$. The pH is adjusted to approximately 10.0 using 25% $NaOCH_3$ solution in $CH_3OH$. The solution is heated to reflux for 2.5 hours, after which time the solvent is removed in vacuo. The residue is washed with cold water and dried in vacuo to yield crude 3-[4-(1-hydroxyiminoethyl)phenyl]-5-allylhydantoin. The hydantoin is purified by recrystallization from $CH_3OH:H_2O$.

EXAMPLE 66

A solution of 0.02 mol p-aminoacetophenone in 40 mL THF is added dropwise to a solution of 0.02 mol of methyl 2-isocyanato-4-methyl-4-pentenoate and 5 mL pyridine in 40 mL THF, and the reaction mixture is stirred for 3 hours. The solvent is then removed by rotary evaporator. The residue is dispersed in 50 mL $CH_3OH$, and 1.53 g hydroxylamine hydrochloride and 6.4 g trimethyl orthoformate are added. The reaction mixture is heated to reflux for 1 hour. The solvent is removed by rotary evaporator to give the product, N-[4-(1-hydroxyiminoethyl)phenyl]-N'-[1-(1-methoxycarbonyl)-3-methyl-3-butenyl]urea.

0.02 mol of this urea is dissolved in 300 mL of $CH_3OH$. The pH is adjusted to approximately 10.0 using 25% $NaOCH_3$ solution in $CH_3OH$. The solution is heated to reflux for 2.5 hours, after which time the

EXAMPLE 67

A solution of 0.02 mol p-aminoacetophenone in 40 mL THF is added dropwise to a solution of 0.02 mol of methyl 2-isocyanato-5-phenyl-4-pentenoate and 5 mL pyridine in 40 mL THF, and the reaction mixture is stirred for 3 hours. The solvent is then removed by rotary evaporator. The residue is dispersed in 50 mL $CH_3OH$, and 1.53 g hydroxylamine hydrochloride and 6.4 g trimethyl orthoformate are added. The reaction mixture is heated to reflux for 1 hour. The solvent is removed by rotary evaporator to give the product, N-[4-(1-hydroxyiminoethyl)phenyl]-N'-[1-(1-methoxycarbonyl)-4-phenyl-3-butenyl]urea.

0.02 mol of this urea is dissolved in 300 mL of $CH_3OH$. The pH is adjusted to approximately 10.0 using 25% $NaOCH_3$ solution in $CH_3OH$. The solution is heated to reflux for 2.5 hours, after which time the solvent is removed in vacuo. The residue is washed with cold water and dried in vacuo to yield crude 3-[4-(1-hydroxyiminoethyl)phenyl]-5-(3-phenylallyl)hydantoin. The hydantoin is purified by recrystallization from $CH_3OH:H_2O$.

EXAMPLE 68

A solution of 0.02 mol p-aminoacetophenone in 40 mL THF is added dropwise to a solution of 0.02 mol of methyl 2-isocyanato-6-acetyloxy-4-hexenoate and 5 mL pyridine in 40 mL THF, and the reaction mixture is stirred for 3 hours. The solvent is then removed by rotary evaporator. The residue is dispersed in 50 mL $CH_3OH$, and 1.53 g hydroxylamine hydrochloride and 6.4 g trimethyl orthoformate are added. The reaction mixture is heated to reflux for 1 hour. The solvent is removed by rotary evaporator to give the product, N-[4-(1-hydroxyiminoethyl)phenyl]-N'-[1-(1-methoxycarbonyl)-5-acetyloxy-3-pentenyl]urea.

0.02 mol of this urea is dissolved in 300 mL of $CH_3OH$. The pH is adjusted to approximately 10.0 using 25% $NaOCH_3$ solution in $CH_3OH$. The solution is heated to reflux for 2.5 hours, after which time the solvent is removed in vacuo. The residue is washed with cold water and dried in vacuo to yield crude 3-[4-(1-hydroxyiminoethyl)phenyl]-5-(4-acetyloxy-2-butenyl)hydantoin. The hydantoin is purified by recrystallization from $CH_3OH:H_2O$.

EXAMPLE 69

A solution of 0.02 mol N-allylglycine ethyl ester, prepared as described by S. B. Hyeon, I. Nagai, H. Tesaka, T. Kajita, and M. Furushima in European Patent Application No. 181,494, in 40 mL of THF is added dropwise to a solution of 0.02 mol of 4-isocyanatoacetophenone, prepared as described by E. E. Kilbourn, D. L. Peardon, and J. E. Ware in U.S. Pat. No. 3,931,203, and 5 mL of pyridine in 40 mL of THF, and the reaction mixture is stirred for 3 hours. The solvent is then removed by rotary evaporator. The residue is dispersed in 50 mL of $CH_3OH$, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminoethyl)phenyl]-N'-allyl-N'-ethoxycarbonylmethylurea.

0.01 mol of this urea is dissolved in 150 mL of $CH_3OH$. The pH is adjusted to approximately 10.0 using 25% $NaOCH_3$ solution in $CH_3OH$. The solution is heated to reflux for 2.5 hours, after which time the solvent is removed in vacuo. The residue is washed with cold water and dried in vacuo to yield crude 1-allyl-3-[4-(1-hydroxyiminoethyl)phenyl]hydantoin. The hydantoin is purified by recrystallization from $CH_3OH:H_2O$.

EXAMPLE 70

A solution of 0.02 mol N-allylalanine ethyl ester, prepared as described by S. B. Hyeon, I. Nagai, H. Iesaka, T. Kajita, and M. Furushima in European Patent Application No. 181,494, in 40 mL of THF is added dropwise to a solution of 0.02 mol of 4-isocyanatopropiophenone, prepared as described by E. E. Kilbourn, D. L. Peardon, and J. E. Ware in U.S. Pat. No. 3,931,203, and 5 mL of pyridine in 40 mL of THF, and the reaction mixture is stirred for 3 hours. The solvent is then removed by rotary evaporator. The residue is dispersed in 50 mL of $CH_3OH$, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminopropyl)phenyl]-N'-allyl-N'-(1-ethoxycarbonylethyl)urea.

0.01 mol of this urea is dissolved in 150 mL of $CH_3OH$. the pH is adjusted to approximately 10.0 using 25% $NaOCH_3$ solution in $CH_3OH$. The solution is heated to reflux for 2.5 hours, after which time the solvent is removed in vacuo. The residue is washed with cold water and dried in vacuo to yield crude 1-allyl-3-[4-(1-hydroxyiminopropyl)phenyl]-5-methylhydantoin. The hydantoin is purified by recrystallization from $CH_3OH: H_2O$.

EXAMPLE 71

A solution of 0.02 mol N-2-butenylglycine ethyl ester, prepared as described by S. B. Hyeon, I. Nagai, H. Iesaka, T. Kajita, and M. Furushima in European patent application No. 181,494, in 40 mL of THF is added dropwise to a solution of 0.02 mol of 4-isocyanatobutyrophenone, prepared as described by E. E. Kilbourn, D. L. Peardon, and J. E. Ware in U.S. Pat. No. 3,931,203, and 5 mL of pyridine in 40 mL of THF, and the reaction mixture is stirred for 3 hours. The solvent is then removed by rotary evaporator. The residue is dispersed in 50 mL of $CH_3OH$, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminobutyl)phenyl]-N'-(2-butenyl)-N'-ethoxycarbonylmethylurea.

0.01 mol of this urea is dissolved in 150 mL of $CH_3OH$. the pH is adjusted to approximately 10.0 using 25% $NaOCH_3$ solution in $CH_3OH$. The solution is heated to reflux for 2.5 hours, after which time the solvent is removed in vacuo. The residue is washed with cold water and dried in vacuo to yield crude 1-(2-butenyl)-3-[4-(1-hydroxyiminobutyl)phenyl]hydantoin. The hydantoin is purified by recrystallization from $CH_3OH: H_2O$.

EXAMPLE 72

A solution of 0.02 mol N-(2-styryl)glycine ethyl ester, prepared as described by A. Padwa, R. Lim, J. G. MacDonald, H. L. Gingrich, and S. M. Kellar in *J. Org. Chem.*, 1985, 50, 3816–3823, in 40 mL of THF is added dropwise to a solution of 0.02 mol of 4-isocyanatoacetophenone and 5 mL of pyridine in 40 mL of THF, and the reaction mixture is stirred for 3 hours. The solvent is then removed by rotary evaporator. The residue is dispersed in 50 mL of $CH_3OH$, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminoethyl)phenyl]-N'-(2-styryl)-N'-ethoxycarbonylmethylurea.

0.01 mol of this urea is dissolved in 150 mL of $CH_3OH$. the pH is adjusted to approximately 10.0 using 25% $NaOCH_3$ solution in $CH_3OH$. The solution is heated to reflux for 2.5 hours, after which time the solvent is removed in vacuo. The residue is washed with cold water and dried in vacuo to yield crude 1-(2-styryl)-3-[4-(1-hydroxyiminoethyl)phenyl]hydantoin. The hydantoin is purified by recrystallization from $CH_3OH$: $H_2O$.

EXAMPLE 73

A solution of 0.02 mol N-(2-styryl)alanine ethyl ester, prepared as described by A. Padwa, R. Lim, J. G. MacDonald, H. L. Gingrich, and S. M. Kellar in *J. Org. Chem.*, 1985, 50, 3816–3823, in 40 mL of THF is added dropwise to a solution of 0.02 mol of 4-isocyanatoacetophenone and 5 mL of pyridine in 40 mL of THF, and the reaction mixture is stirred for 3 hours. The solvent is then removed by rotary evaporator. The residue is dispersed in 50 mL of $CH_3OH$, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminoethyl)phenyl]-N'-2-styryl-N'-(1-ethoxycarbonyl)ethylurea.

0.01 mol of this urea is dissolved in 150 mL of $CH_3OH$. the pH is adjusted to approximately 10.0 using 25% $NaOCH_3$ solution in $CH_3OH$. The solution is heated to reflux for 2.5 hours, after which time the solvent is removed in vacuo. The residue is washed with cold water and dried in vacuo to yield crude 1-(2-styryl)-3-[4-(1-hydroxyiminoethyl)phenyl]-5-methylhydantoin. The hydantoin is purified by recrystallization from $CH_3OH$: $H_2O$.

EXAMPLE 74

A solution of 0.06 mol of N-(2-allylphenyl)alanine, prepared as described by A. Padwa, H. L. Gingrich, and R. Lim in *J. Org. Chem.*, 1982, 47, 2447–2456, and 0.066 mol of HCl in 100 mL of $CH_3OH$ is stirred at reflux for 8 hours. The solution is then cooled and treated with 0.066 mol of sodium bicarbonate. The solvent is removed by rotary evaporator, and the residue is dissolved in diethyl ether, filtered, dried over $MgSO_4$, and filtered. The solvent is removed by rotary evaporator to give N-(2-allylphenyl)alanine methyl ester.

A solution of 0.02 mol N-(2-allylphenyl)alanine methyl ester in 40 mL of THF is added dropwise to a solution of 0.02 mol of 4-isocyanatoacetophenone and 5 mL of pyridine in 40 mL of THF, and the reaction mixture is stirred for 3 hours. The solvent is then removed by rotary evaporator. The residue is dispersed in 50 mL of $CH_3OH$, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminoethyl)phenyl]-N'-(2-allylphenyl)-N'-(1-methoxycarbonyl)ethylurea.

0.01 mol of this urea is dissolved in 150 mL of $CH_3OH$. the pH is adjusted to approximately 10.0 using 25% $NaOCH_3$ solution in $CH_3OH$. The solution is heated to reflux for 2.5 hours, after which time the solvent is removed in vacuo. The residue is washed with cold water and dried in vacuo to yield crude 1-(2-allylphenyl)-3-[4-(1-hydroxyiminoethyl)phenyl]-5-methylhydantoin. The hydantoin is purified by recrystallization from $CH_3OH$: $H_2O$.

EXAMPLE 75

A solution of 0.06 mol of N-(2-allylphenyl)phenylglycine, prepared as described by A. Padwa, H. L. Gingrich, and R. Lim in *J. Org. Chem.*, 1982, 47, 2447–2456, and 0.066 mol of HCl in 100 mL of $CH_3OH$ is stirred at reflux for 8 hours. The solution is then cooled and treated with 0.066 mol of sodium bicarbonate. The solvent is removed by rotary evaporator, and the residue is dissolved in diethyl ether, filtered, dried over $MgSO_4$, and filtered. The solvent is removed by rotary evaporator to give N-(2-allylphenyl)phenylglycine methyl ester.

A solution of 0.02 mol N-(2-allylphenyl)phenylglycine methyl ester in 40 mL of THF is added dropwise to a solution of 0.02 mol of 4-isocyanatoacetophenone and 5 mL of pyridine in 40 mL of THF, and the reaction mixture is stirred for 3 hours. The solvent is then removed by rotary evaporator. The residue is dispersed in 50 mL of $CH_3OH$, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminoethyl)phenyl]-N'-(2-allylphenyl)-N'-(methoxycarbonyl)phenylmethylurea.

0.01 mol of this urea is dissolved in 150 mL of $CH_3OH$. the pH is adjusted to approximately 10.0 using 25% $NaOCH_3$ solution in $CH_3OH$. The solution is heated to reflux for 2.5 hours, after which time the solvent is removed in vacuo. The residue is washed with cold water and dried in vacuo to yield crude 1-(2-allylphenyl)-3-[4-(1-hydroxyiminoethyl)phenyl]-5-phenylhydantoin. The hydantoin is purified by recrystallization from $CH_3OH$: $H_2O$.

EXAMPLE 76

A solution of 0.06 mol of N-(2-allylphenyl)glycine, prepared as described by A. Padwa, R. Lim, J. G. MacDonald, H. L. Gingrich, and S. M. Kellar in *J. Org. Chem.*, 1985, 50, 3816–3823, and 0.066 mol of HCl in 100 mL of $CH_3OH$ is stirred at reflux for 8 hours. The solution is then cooled and treated with 0.066 mol of sodium bicarbonate. The solvent is removed by rotary evaporator, and the residue is dissolved in diethyl ether, filtered, dried over $MgSO_4$, and filtered. The solvent is removed by rotary evaporator to give N-(2-allylphenyl)glycine methyl ester.

A solution of 0.02 mol N-(2-allylphenyl)glycine methyl ester in 40 mL of THF is added dropwise to a solution of 0.02 mol of 4-isocyanatoacetophenone and 5 mL of pyridine in 40 mL of THF, and the reaction mixture is stirred for 3 hours. The solvent is then removed by rotary evaporator. The residue is dispersed in 50 mL of CH$_3$OH, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminoethyl)phenyl]-N'-(2-allylphenyl)-N'-methoxycarbonylmethylurea.

0.01 mol of this urea is dissolved in 150 mL of CH$_3$OH. the pH is adjusted to approximately 10.0 using 25% NaOCH$_3$ solution in CH$_3$OH. The solution is heated to reflux for 2.5 hours, after which time the solvent is removed in vacuo. The residue is washed with cold water and dried in vacuo to yield crude 1-(2-allylphenyl)-3-[4-(1-hydroxyiminoethyl)phenyl]hydantoin. The hydantoin is purified by recrystallization from CH$_3$OH: H$_2$O.

EXAMPLE 77

A solution of 0.06 mol of N-(allyloxycarbonyl)alanine, prepared as described by H. Kunz and C. Unverzagt in *Angew. Chem. Int. Ed. Engl.*, 1984, 23, 436–437, and 0.066 mol of HCl in 100 mL of CH$_3$OH is stirred at reflux for 8 hours. The solution is then cooled and treated with 0.066 mol of sodium bicarbonate. The solvent is removed by rotary evaporator, and the residue is dissolved in diethyl ether, filtered, dried over MgSO$_4$, and filtered. The solvent is removed by rotary evaporator to give N-(allyloxycarbonyl)alanine methyl ester.

A solution of 0.02 mol N-(allyloxycarbonyl)alanine methyl ester in 40 mL of THF is added dropwise to a solution of 0.02 mol of 4-isocyanatoacetophenone and 5 mL of pyridine in 40 mL of THF, and the reaction mixture is stirred for 3 hours. The solvent is then removed by rotary evaporator. The residue is dispersed in 50 mL of CH$_3$OH, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminoethyl)phenyl]-N'-allyloxycarbonyl-N'-(1-methoxycarbonyl)ethylurea.

0.01 mol of this urea is dissolved in 150 mL of CH$_3$OH. the pH is adjusted to approximately 10.0 using 25% NaOCH$_3$ solution in CH$_3$OH. The solution is heated to reflux for 2.5 hours, after which time the solvent is removed in vacuo. The residue is washed with cold water and dried in vacuo to yield crude 1-allyloxycarbonyl-3-[4-(1-hydroxyiminoethyl)phenyl]-5-methylhydantoin. The hydantoin is purified by recrystallization from CH$_3$OH: H$_2$O.

EXAMPLE 78

A solution of 0.06 mol of N-(allyloxycarbonyl)phenylalanine, prepared as described by H. Kunz and C. Unverzagt in *Angew. Chem. Int. Ed. Engl.*, 1984, 23, 436–437, and 0.066 mol of HCl in 100 mL of CH$_3$OH is stirred at reflux for 8 hours. The solution is then cooled and treated with 0.066 mol of sodium bicarbonate. The solvent is removed by rotary evaporator, and the residue is dissolved in diethyl ether, filtered, dried over MgSO$_4$, and filtered. The solvent is removed by rotary evaporator to give N-(allyloxycarbonyl)phenylalanine methyl ester.

A solution of 0.02 mol N-(allyloxycarbonyl)phenylalanine methyl ester in 40 mL of THF is added dropwise to a solution of 0.02 mol of 4-isocyanatoacetophenone and 5 mL of pyridine in 40 mL of THF, and the reaction mixture is stirred for 3 hours. The solvent is then removed by rotary evaporator. The residue is dispersed in 50 mL of CH$_3$OH, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminoethyl)phenyl]-N'-allyloxycarbonyl-N'-[(1-methoxycarbonyl)-2-phenylethyl]urea.

0.01 mol of this urea is dissolved in 150 mL of CH$_3$OH. the pH is adjusted to approximately 10.0 using 25% NaOCH$_3$ solution in CH$_3$OH. The solution is heated to reflux for 2.5 hours, after which time the solvent is removed in vacuo. The residue is washed with cold water and dried in vacuo to yield crude 1-allyloxycarbonyl-3-[4-(1-hydroxyiminoethyl)phenyl]-5-benzylhydantoin. The hydantoin is purified by recrystallization from CH$_3$OH: H$_2$O.

EXAMPLE 79

A solution of 0.06 mol of N-(allyloxycarbonyl)methionine, prepared as described by H. Kunz and C. Unverzagt in *Angew. Chem. Int. Ed. Engl.*, 1984, 23, 436–437, and 0.066 mol of HCl in 100 mL of CH$_3$OH is stirred at reflux for 8 hours. The solution is then cooled and treated with 0.066 mol of sodium bicarbonate. The solvent is removed by rotary evaporator, and the residue is dissolved in diethyl ether, filtered, dried over MgSO$_4$, and filtered. The solvent is removed by rotary evaporator to give N-(allyloxycarbonyl)methionine methyl ester.

A solution of 0.02 mol N-(allyloxycarbonyl)methionine methyl ester in 40 mL of THF is added dropwise to a solution of 0.02 mol of 4-isocyanatoacetophenone and 5 mL of pyridine in 40 mL of THF, and the reaction mixture is stirred for 3 hours. The solvent is then removed by rotary evaporator. The residue is dispersed in 50 mL of CH$_3$OH, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminoethyl)phenyl]-N'-allyloxycarbonyl-N'-[(1-methoxycarbonyl)-3-(methylthio)propyl]urea.

0.01 mol of this urea is dissolved in 150 mL of CH$_3$OH. the pH is adjusted to approximately 10.0 using 25% NaOCH$_3$ solution in CH$_3$OH. The solution is heated to reflux for 2.5 hours, after which time the solvent is removed in vacuo. The residue is washed with cold water and dried in vacuo to yield crude 1-allyloxycarbonyl-3-[4-(1-hydroxyiminoethyl)phenyl]-5-(2-methylthioethyl)hydantoin. The hydantoin is purified by recrystallization from CH$_3$OH: H$_2$O.

EXAMPLE 80

A solution of 0.06 mol of N-(allyloxycarbonyl)glycine, prepared as described by F. Guibe, O. Dangles, and G. Balavione in *Tetrahedron Letters*, 1986, 27, 2365–2368, and 0.066 mol of HCl in 100 mL of CH$_3$OH is stirred at reflux for 8 hours. The solution is then cooled and treated with 0.066 mol of sodium bicarbonate. The solvent is removed by rotary evaporator, and the residue is dissolved in diethyl ether, filtered, dried over MgSO$_4$, and filtered. The solvent is removed by rotary evaporator to give N-(allyloxycarbonyl)glycine methyl ester.

A solution of 0.02 mol N-(allyloxycarbonyl)glycine methyl ester in 40 mL of THF is added dropwise to a solution of 0.02 mol of 4-isocyanatoacetophenone and 5 mL of pyridine in 40 mL of THF, and the reaction mixture is stirred for 3 hours. The solvent is then removed by rotary evaporator. The residue is dispersed in 50 mL of CH$_3$OH, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminoethyl)phenyl]-N'-allyloxycarbonyl-N'-methoxycarbonylmethylurea.

0.01 mol of this urea is dissolved in 150 mL of CH$_3$OH. the pH is adjusted to approximately 10.0 using 25% NaOCH$_3$ solution in CH$_3$OH. The solution is heated to reflux for 2.5 hours, after which time the solvent is removed in vacuo. The residue is washed with cold water and dried in vacuo to yield crude 1-allyloxycarbonyl-3-[4-(1-hydroxyiminoethyl)phenyl]-hydantoin. The hydantoin is purified by recrystallization from CH$_3$OH: H$_2$O.

EXAMPLE 81

A solution of 0.06 mol of N-(allyloxycarbonyl)leucine, prepared as described by F. Guibe, O. Dangles, and G. Balavione in *Tetrahedron Letters*, 1986, 27, 2365–2368, and 0.066 mol of HCl in 100 mL of CH$_3$OH is stirred at reflux for 8 hours. The solution is then cooled and treated with 0.066 mol of sodium bicarbonate. The solvent is removed by rotary evaporator, and the residue is dissolved in diethyl ether, filtered, dried over MgSO$_4$, and filtered. The solvent is removed by rotary evaporator to give N-(allyloxycarbonyl)leucine methyl ester.

A solution of 0.02 mol N-(allyloxycarbonyl)leucine methyl ester in 40 mL of THF is added dropwise to a solution of 0.02 mol of 4-isocyanatoacetophenone and 5 mL of pyridine in 40 mL of THF, and the reaction mixture is stirred for 3 hours. The solvent is then removed by rotary evaporator. The residue is dispersed in 50 mL of CH$_3$OH, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminoethyl)phenyl]-N'-allyloxycarbonyl-N'-[(1-methoxycarbonyl)-3-methylbutyl]urea.

0.01 mol of this urea is dissolved in 150 mL of CH$_3$OH. the pH is adjusted to approximately 10.0 using 25% NaOCH$_3$ solution in CH$_3$OH. The solution is heated to reflux for 2.5 hours, after which time the solvent is removed in vacuo. The residue is washed with cold water and dried in vacuo to yield crude 1-allyloxycarbonyl-3-[4-(1-hydroxyiminoethyl)phenyl]-5-sec-butylhydantoin. The hydantoin is purified by recrystallization from CH$_3$OH: H$_2$O.

EXAMPLE 82

A solution of 0.02 mol methyl 2-amino-4-pentenoate in 40 mL of THF is added dropwise to a solution of 0.02 mol of 4-isocyanatoacetophenone and 5 mL of pyridine in 40 mL of THF, and the reaction mixture is stirred for 3 hours. The solvent is then removed by rotary evaporator. The residue is dispersed in 50 mL of CH$_3$OH, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminoethyl)phenyl]-N'-[(1-methoxycarbonyl)-3-butenyl]urea.

0.01 mol of this urea is dissolved in 150 mL of CH$_3$OH. the pH is adjusted to approximately 10.0 using 25% NaOCH$_3$ solution in CH$_3$OH. The solution is heated to reflux for 2.5 hours, after which time the solvent is removed in vacuo. The residue is washed with cold water and dried in vacuo to yield crude 3-[4-(1-hydroxyiminoethyl)phenyl]-5-allylhydantoin. The hydantoin is purified by recrystallization from CH$_3$OH: H$_2$O.

EXAMPLE 83

A solution of 0.02 mol methyl 2-amino-4-methyl-4-pentenoate in 40 mL of THF is added dropwise to a solution of 0.02 mol of 4-isocyanatoacetophenone and 5 mL of pyridine in 40 mL of THF, and the reaction mixture is stirred for 3 hours. The solvent is then removed by rotary evaporator. The residue is dispersed in 50 mL of CH$_3$OH, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminoethyl)phenyl]-N'-[(1-methoxycarbonyl)-3-methyl-3-butenyl]urea.

0.01 mol of this urea is dissolved in 150 mL of CH$_3$OH. the pH is adjusted to approximately 10.0 using 25% NaOCH$_3$ solution in CH$_3$OH. The solution is heated to reflux for 2.5 hours, after which time the solvent is removed in vacuo. The residue is washed with cold water and dried in vacuo to yield crude 3-[4-(1-hydroxyiminoethyl)phenyl]-5-(2-methylallyl)hydantoin. The hydantoin is purified by recrystallization from CH$_3$OH: H$_2$O.

EXAMPLE 84

A solution of 0.02 mol methyl 2-amino-5-phenyl-4-pentenoate in 40 mL of THF is added dropwise to a solution of 0.02 mol of 4-isocyanatoacetophenone and 5 mL of pyridine in 40 mL of THF, and the reaction mixture is stirred for 3 hours. The solvent is then removed by rotary evaporator. The residue is dispersed in 50 mL of CH$_3$OH, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminoethyl)phenyl]-N'-[(1-methoxycarbonyl)-4-phenyl-3-butenyl]urea.

0.01 mol of this urea is dissolved in 150 mL of CH$_3$OH. the pH is adjusted to approximately 10.0 using 25% NaOCH$_3$ solution in CH$_3$OH. The solution is heated to reflux for 2.5 hours, after which time the solvent is removed in vacuo. The residue is washed with cold water and dried in vacuo to yield crude 3-[4-(1-hydroxyiminoethyl)phenyl]-5-(3-phenylallyl)hydantoin. The hydantoin is purified by recrystallization from CH$_3$OH: H$_2$O.

EXAMPLE 85

A solution of 0.02 mol methyl 2-amino-6-acetyloxy-4-hexenoate in 40 mL of THF is added dropwise to a solution of 0.02 mol of 4-isocyanatoacetophenone and 5 mL of pyridine in 40 mL of THF, and the reaction mixture is stirred for 3 hours. The solvent is then removed by rotary evaporator. The residue is dispersed in 50 mL of CH$_3$OH, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminoethyl)phenyl]-N'-[(1-methoxycarbonyl)-5-acetyloxy-3-pentenyl]urea.

0.01 mol of this urea is dissolved in 150 mL of $CH_3OH$. the pH is adjusted to approximately 10.0 using 25% $NaOCH_3$ solution in $CH_3OH$. The solution is heated to reflux for 2.5 hours, after which time the solvent is removed in vacuo. The residue is washed with cold water and dried in vacuo to yield crude 3-[4-(1-hydroxyiminoethyl)phenyl]-5-(4-acetyloxy-2-butenyl)hydantoin. The hydantoin is purified by recrystallization from $CH_3OH$: $H_2O$.

EXAMPLE 85

A solution of AIBN (0.001 mol) and 3-[4-allyloxyiminomethyl)phenyl]hydantoin (0.01 mol) in 10 mL of toluene is stirred under a nitrogen atmosphere at 80° C. for 48 hours. The solvent is removed to leave a polymeric material.

EXAMPLE 86

A solution of AIBN (0.001 mol) and 1-allyl-3-[4-allyloxyiminomethyl)phenyl]hydantoin (0.01 mol) in 10 mL of toluene is stirred under a nitrogen atmosphere at 80° C. for 48 hours. The solvent is removed to leave a polymeric material.

EXAMPLE 87

A solution of AIBN (0.001 mol) and 1-allyl-3-[4-(1-hydroxyiminoethyl)phenyl]hydantoin (0.01 mol) in 10 mL of toluene is stirred under a nitrogen atmosphere at 80° C. for 48 hours. The solvent is removed to leave a polymeric material.

EXAMPLE 88

A solution of AIBN (0.001 mol) and 3-[4-hydroxyiminomethyl)phenyl]-5-allylhydantoin (0.01 mol) in 10 mL of toluene is stirred under a nitrogen atmosphere at 80° C. for 48 hours. The solvent is removed to leave a polymeric material.

EXAMPLE 89

A solution of AIBN (0.001 mol) and 1-allyloxycarbonyl-3-[4-(1-hydroxyiminoethyl)phenyl]hydantoin (0.01 mol) in 10 mL of toluene is stirred under a nitrogen atmosphere at 80° C. for 48 hours. The solvent is removed to leave a polymeric material.

As will be evident to those skilled in the art, various modifications of this invention can be made or followed in the light of the foregoing disclosure and discussion without departing from the spirit and scope of the disclosure or from the scope of the claims.

We claim:

1. A compound of the formula,

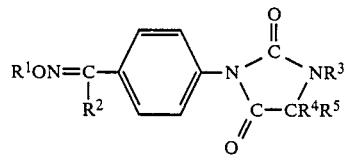

Formula 1 where each of $R^1$, $R^2$, $R^3$, $R^4$ and $R^5$ has zero to 10 C atoms, and no acetylenic unsaturation; each of $R^1$, $R^2$ and $R^3$ is independently selected from H and hydrocarbyl; each of $R^4$ and $R^5$ is independently selected from H, hydrocarbyl and hydrocarbyl substituted with a group selected from:

hydrocarbylcarbonylamino, di(hydrocarbylcarbonyl)amino, N-hydrocarbylcarbonyl(N-hydrocarbyl)amino, formylamino, diformylamino, and formyl(N-hydrocarbyl)amino, hydrocarbyloxy, hydrocarbylthio, formyl, formylthio, hydrocarbylcarbonyloxy, hydrocarbylcarbonylthio, hydrocarbyl carboxyl, hydrocarbyl thiocarboxyl, hydrocarbylamino, dihydrocarbylamino, hydrocarbylcarbonyl, 3-indolyl, 3-(1-hydrocarbyl)indolyl, 3-(1-hydrocarbylcarbonyl)indolyl, 3-(1-formyl)indolyl, carbamoyl, hydrocarbylcarbamoyl, dihydrocarbylcarbamoyl, 5-imidazolyl, 5-(3-hydrocarbyl)imidazolyl, 5-(3-hydrocarbylcarbonyl)imidazolyl, and 5-(3-formyl)imidazolyl, and where at least one of $R^1$, $R^2$, $R^3$, $R^4$ and $R^5$ contains olefinic unsaturation.

2. A polymer of a compound of claim 1.

* * * * *